United States Patent
Kang et al.

(10) Patent No.: US 8,940,233 B2
(45) Date of Patent: Jan. 27, 2015

(54) CARTRIDGE FOR APPARATUS FOR CHEMICALLY ANALYZING BLOOD AND APPARATUS USING THE SAME

(75) Inventors: Tae Young Kang, Seoul (KR); Heejun Lee, Seoul (KR); Jeonghan Ha, Seoul (KR); Jungwon Shin, Seoul (KR); Hakhyun Nam, Seoul (KR); Geun Sig Cha, Seoul (KR)

(73) Assignee: I-Sens, Inc., Seoul (KR)

( * ) Notice: Subject to any disclaimer, the term of this patent is extended or adjusted under 35 U.S.C. 154(b) by 622 days.

(21) Appl. No.: 12/739,686

(22) PCT Filed: Oct. 30, 2008

(86) PCT No.: PCT/KR2008/006429
§ 371 (c)(1),
(2), (4) Date: Apr. 23, 2010

(87) PCT Pub. No.: WO2009/057969
PCT Pub. Date: May 7, 2009

(65) Prior Publication Data
US 2011/0195490 A1      Aug. 11, 2011

(30) Foreign Application Priority Data
Nov. 1, 2007    (KR) ................. 10-2007-0110990

(51) Int. Cl.
*C12Q 1/68*       (2006.01)
*G01N 21/00*      (2006.01)
*G01N 33/00*      (2006.01)
*G01N 33/49*      (2006.01)
*G01N 35/00*      (2006.01)

(52) U.S. Cl.
CPC .... *G01N 33/492* (2013.01); *G01N 2035/00089* (2013.01); *G01N 2035/00148* (2013.01)
USPC ................ 422/68.1; 422/50; 422/63; 422/64; 422/65; 422/67; 422/73

(58) Field of Classification Search
CPC ........... A61B 5/15186; G01N 27/3272; G01N 2001/1056; G01N 2001/149; G01N 2035/0465; G01N 33/48785; G01N 2030/285; G01N 2030/8822; G01N 2035/00089; G01N 2035/00148; G01N 30/64; B01L 2200/026; B01L 3/567
USPC .................................. 422/63, 64, 65, 68.1, 50
See application file for complete search history.

(56) References Cited

U.S. PATENT DOCUMENTS

| 4,849,340 A * | 7/1989 | Oberhardt ....................... 435/13 |
| 5,325,853 A * | 7/1994 | Morris et al. ............. 204/403.02 |
| 6,066,243 A * | 5/2000 | Anderson et al. .......... 422/82.01 |
| 2003/0224523 A1 | 12/2003 | Thornberg et al. |

FOREIGN PATENT DOCUMENTS

| KR | 10-0893275 A | 4/2009 |
| WO | WO-02-078533 A2 | 10/2002 |

* cited by examiner

*Primary Examiner* — Dean Kwak
(74) *Attorney, Agent, or Firm* — Rabin & Berdo, P.C.

(57) ABSTRACT

A cartridge for an apparatus for analyzing blood chemistry includes an apparatus frame having a compartment; a cartridge that is inserted into the compartment of the apparatus frame and includes a sensor card, a solution valve unit, and a blood introducing unit; a controller that receives a signal generated from the sensor card and processes the signal; a lever for the blood introducing unit connected to the apparatus frame; a power transmitting unit that is provided to the apparatus frame and transmits power of the lever for the blood introducing unit to open/close the blood introducing unit of the cartridge; a solution transporting unit that is provided to the apparatus frame and transports the solutions; and a driving unit that actuates the solution valve unit of the cartridge by the controller and opens or closes the tubing flowing of the solutions.

10 Claims, 13 Drawing Sheets

CARTRIDGE FOR APPARATUS FOR CHEMICALLY ANALYZING BLOOD AND APPARATUS USING THE SAME

TECHNICAL FIELD

The present invention relates to a cartridge for an apparatus for analyzing blood chemistry and an apparatus using the same. More particularly, the present invention relates to a cartridge for an apparatus for analyzing blood chemistry that is used for medical treatment, and automatically analyzes and records data needed for medical service, such as the concentrations of electrolytes ($Na^+$, $K^+$, $Cl^-$ etc.), gases ($PO_2$, $PCO_2$), and metabolites (glucose, lactate, urea), or the volume ratio of red blood cells contained in blood.

BACKGROUND ART

In general, the concentrations of electrolytes, the partial pressures of gases, and the concentrations of metabolites or the volume ratio of the red blood cells in blood maintain homeostasis in a human body, and concentration imbalance causes various diseases with excessive or lack of concentrations thereof. Therefore, prompt measurement of the concentrations of electrolytes, the partial pressures of gases, and the concentrations of metabolites or the volume ratio of the red blood cells in blood helps a medical team quickly estimate a disorder of a human body or progress of a disease due to bionic imbalance. Equipment for measuring the concentrations of ions of electrolytes, gas, and metabolites or the volume ratio of the red blood cells in blood may include a blood introducing unit that supplies blood, a sensing unit that includes a sensor, a solution supplier that supplies a solution to the sensor, a data process unit, and a plurality of driving sources. These apparatuses for analyzing blood chemistry in the related art have heavy and complicate structures for characteristics of mechanical apparatuses, such that they can only be used in specific test rooms, having a limit on the space for use. In particular, a test is performed in a test room equipped with a blood analysis system, even though a medical team needs to quickly obtain needed data at any place where a patient is, for characteristics of the field of medical treatment. Further, since the blood analysis systems need to periodically replace various solutions and sensors in the related art, they are inconvenient in considering maintenance thereof, and a cartridge type blood analysis system including a solution, a sensor, and a blood introducing unit in one cartridge has been proposed to overcome the problem. However, a reagent solution may leak when being alternatively supplied to the sensing unit in the cartridge, such that reliability of measured data and the commercial value are reduced.

DETAILED DESCRIPTION

Technical Problem

The present invention has been made in an effort to provide a cartridge for an apparatus for analyzing blood chemistry and an apparatus using the same having advantages of having a small portable structure to be used, in addition to on a table, anywhere a patient is, such as an operating room, a recovery room, an emergency room, a diagnosis-examination room, an ambulance, a battlefield, and a field needing emergency medical treatment, and analyzing the concentrations of electrolytes, the partial pressures of gases, and the concentrations of metabolites or the volume ratio of red blood cells contained in blood of a patient to allow a medical team to quickly and easily check the condition of the patient and provide appropriate medical service.

Further, the present invention provides a cartridge for an apparatus for analyzing blood chemistry and an apparatus using the same that has a relatively small structure with good durability, such that the manufacturing cost is reduced and productivity is improved. Further, the present invention provides a cartridge for an apparatus for analyzing blood chemistry and an apparatus using the same that can be easily used and prevent a solution from leaking, such that commercial value is improved.

Technical Solution

An exemplary embodiment of the present invention provides an apparatus for analyzing blood chemistry that preferably includes: an apparatus frame having a compartment; a cartridge that is inserted into the compartment of the apparatus frame and includes solution bags that contains solutions, a solution valve unit that allows or blocks the flow of the solutions, and a blood introducing unit; a sensor card that is disposed in the cartridge or in the apparatus frame and measures the concentrations of electrolytes, the partial pressures of gases, and the concentrations of metabolites, or the volume ratio of the red blood cells contained in blood supplied through the blood introducing unit; a controller that receives signals generated from the sensor card and processes the signals; a lever for the blood introducing unit that is connected to the apparatus frame; a power transmitting unit that is provided to the apparatus frame and transmits power from the lever to open or close the blood introducing unit; a solution transporting unit that is provided to the apparatus frame and transports the solutions in the solution bags; and driving units that actuates the solution valve unit of the cartridge by the controller and opens or closes the tubing flowing of the solutions It is preferable that the apparatus for analyzing blood chemistry includes an output unit that outputs data processed by the controller and the output unit includes a display and a printer, both of which are integrated in the apparatus.

In the apparatus for analyzing blood chemistry, it is preferable that a part of the controller that receives signals generated from the sensor card and processes the signals is electrically isolated from a part of the controller that controls the solution transporting unit and the driving units.

In the apparatus for analyzing blood chemistry, it is preferable that the signals generated from the sensor card that the controller receives and processes are electrically isolated between the signals depending on the type of the signals It is preferable that the apparatus frame is provided with a cartridge door 1 that is fastened by a hinge to the frame and is equipped with a cartridge door lock to lock the cartridge door to the frame and a cartridge door lock sensor to sense the locking status of the door lock and transmits a sensed signal to the controller.

It is preferable that the apparatus frame is provided with a lever lock that locks the lever for the blood introducing unit and a sensing unit that senses the locking status of the lever lock and transmits a sensed signal to the controller.

It is preferable the apparatus frame is provided with a sensing unit that detects the operation of the driving unit and transmits a detected signal to the controller.

It is preferable that the lever for blood introducing unit is a cover for the blood introducing unit that is composed of a magnifier at the center thereof.

It is preferable that the solution tubing connectors have a plurality of inlets connected to the solution bags through tubing and an outlet connected to the inlets to supply the solutions to the sensor card through the blood introducing unit.

It is preferable that the apparatus frame is provided with a heater block equipped with a heater to maintain the temperature of the sensor card constant.

It is preferable that the cartridge is provided with a waste container connected with the sensor card through tubing.

The present invention provides an apparatus for analyzing blood chemistry, including: a apparatus frame having a compartment; a cartridge that includes a cartridge case received in the apparatus frame, a sensor card provided in the cartridge case and detecting concentrations of electrolytes, the partial pressures of gases, and the concentrations of metabolites, or the volume ratio of the red blood cells contained in blood, solution bags included in the cartridge case and containing solutions flowing to the sensor card by a solution transporting unit, a solution tubing connector that is connected through tubing to each of the solution bags, a solution valve unit allowing or blocking the flowing of the solutions in the solution bags to the sensor card, and a blood introducing unit that is connected/disconnected to the solution tubing connecter and is connected to the sensor card through tubing to supply blood or the solutions to the sensor card; a controller that receives a signal generated from the sensor card and processes the signal; a lever for the blood introducing unit that is connected to the apparatus frame; a power transmitting unit that is provided to the apparatus frame and transmits power of the lever for the blood introducing unit to open/close the blood introducing unit of the cartridge; a solution transporting unit that is provided to the apparatus frame and transports the solutions in the solution bags; and driving units that actuates the solution valve unit of the cartridge by the controller and opens or closes the tubing flowing of the solutions The present invention provides a cartridge for an apparatus for analyzing blood chemistry, including: a cartridge case having a space; a sensor card provided in the cartridge case and detecting concentrations of electrolytes, the partial pressures of gases, and the concentrations of metabolites, or the volume ratio of the red blood cells contained in blood; solution bags placed in the space of the cartridge case and of which transported to the sensor card by the solution transporting unit; a waste container placed in the space of the cartridge case and connected to the sensor card through a tubing; a solution tubing connector that is connected through a tubing to each of the solution bags; a solution valve unit allowing or blocking the flow of the solutions in the solution bags to the sensor card; and a blood introducing unit that is connected/disconnected to the solution tubing connectors and is connected to the sensor card through tubing to supply blood or the solutions to the sensor card.

It is preferable that the solution tubing connector has a plurality of inlets connected to the solution bags through tubing, and an outlet connected to the inlets to supply the solutions to the sensor card from the blood introducing unit.

It is preferable that the solution valve unit includes: pressing members that are disposed over the tubing connecting between the solution bags and the solution tubing connector and close the tubing by applying pressure to the tubing and open the tubing by releasing the pressure applied to the tubing, and elastic members that applies elastic forces to the pressing members to maintain the pressure applied to the tubing.

It is preferable that the pressing member has a body, a head formed at an end of the body to hold the elastic member, and an extension part at the other end of the body and having a tubing insertion hole.

Advantageous Effects

According to the present invention, since the apparatus has a small portable structure, a medical team can quickly measure the concentrations of electrolytes, the partial pressures of gases, and the concentrations of metabolites, or the volume ratio of red blood cells contained in blood of a patient anywhere the medical team is needed, without requiring a space, and can quickly make a decision based thereon.

Further, according to the present invention, productivity and commercial value are improved while easy to use.

BEST MODE

Hereinafter, preferred exemplary embodiments of the invention are described with reference to the accompanying drawings.

Figure 1:
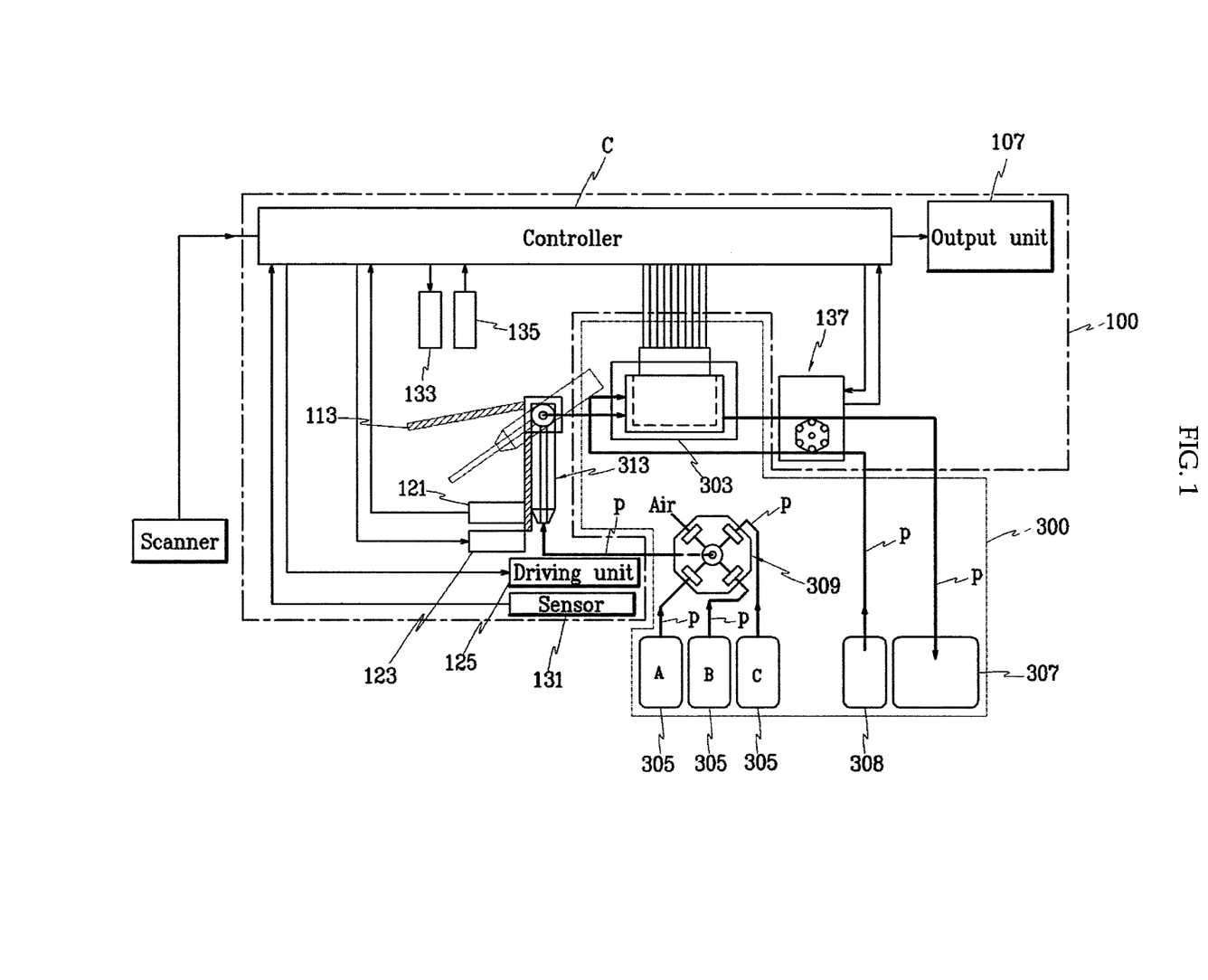
FIG. 1 is a schematic diagram illustrating the configuration of an exemplary embodiment of the present invention.
Figure 2:
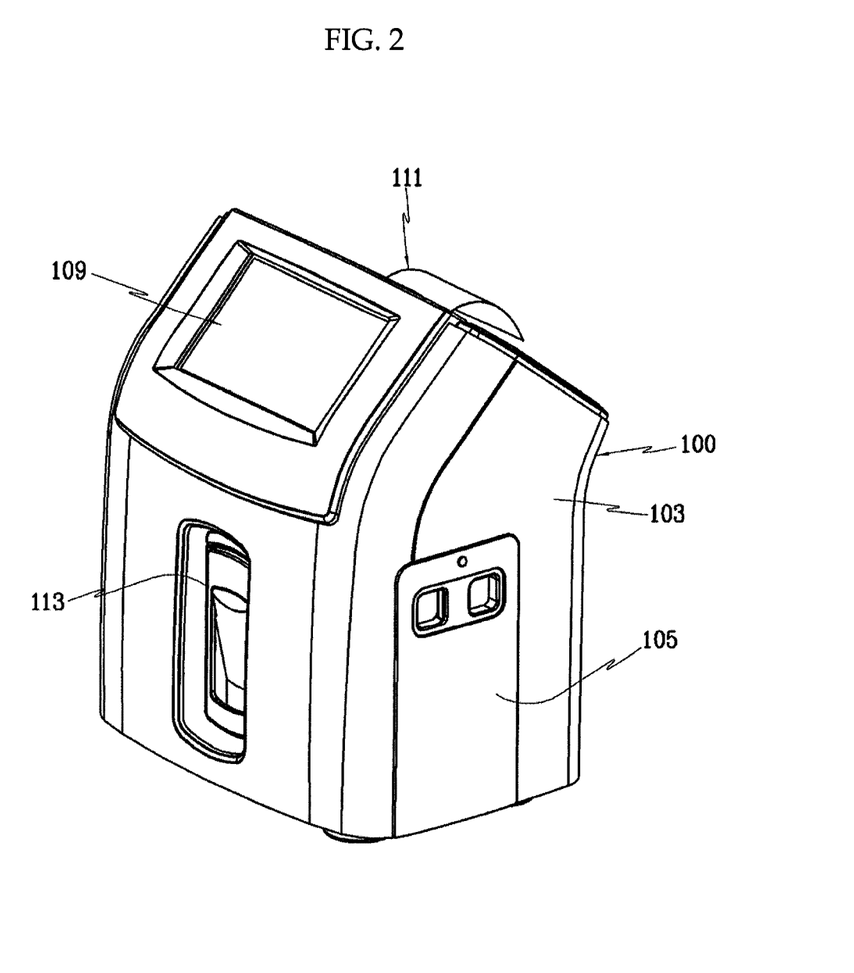
FIG. 2 is a perspective view illustrating an exemplary embodiment of the present invention.
Figure 3:
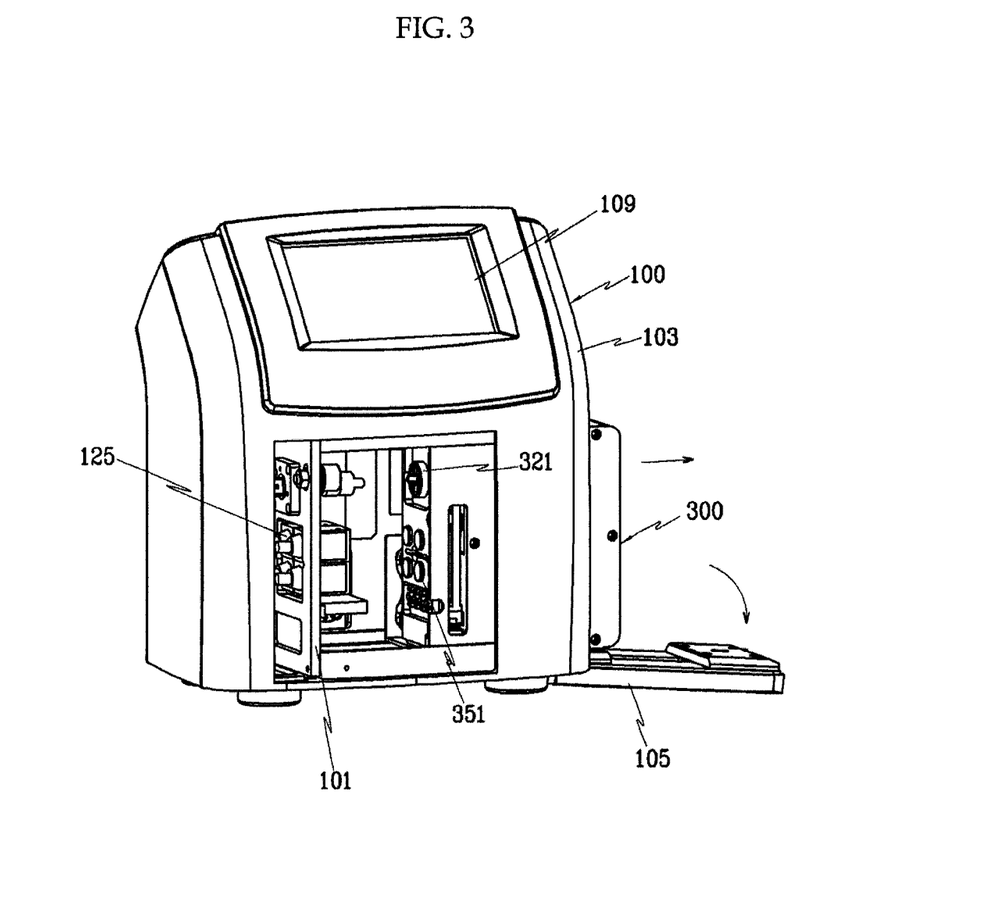
FIG. 3 is an exploded view illustrating a portion of the main part according to an exemplary embodiment of the present invention.

FIG. 1 is a schematic diagram illustrating the configuration of an exemplary embodiment of the present invention, FIG. 2 is perspective view illustrating an exemplary embodiment of the present invention, and FIG. 3 is an exploded view of the main part of FIG. 2, illustrating the main configuration of an apparatus for analyzing blood chemistry. The apparatus for analyzing blood chemistry includes a main body 100 and a cartridge 300. The main body 100, as shown in FIG. 3, includes an apparatus frame 101 forming a compartment therein and a case 103 combined with the apparatus frame 101 to form the outer shape. In the description of an exemplary embodiment of the present invention, installing constituent elements to the apparatus frame 101 has the same meaning as installing the constituent element in the case 103, and the invention is not limited to those shown in the drawing.

The apparatus frame 101, which is a framework of the apparatus for analyzing blood chemistry, has a space where the cartridge 300 is inserted and fixed to a predetermined position. Further, the apparatus frame 101 is provided with a cartridge door 105 that separates the cartridge 300 from the outside after the cartridge 300 is received. The cartridge door 105 is connected to the apparatus frame 101 by a common connecting means, such as a hinge, to be used to insert or draw out the cartridge 300. The cartridge door 105 is provided in this exemplary embodiment of the present invention; however, the cartridge door 105 may not be provided, depending on the design. Further, a controller C and a data output unit 107 that is controlled by the controller C are connected to the apparatus frame 101. The data output unit 107, which is a device for display data processed by the controller C to allow a user to recognize the data, includes a common display 109 and a printer 111. The data output unit 107 is integrally formed with the main body 100. The main body 100 can be used without requiring a space when a medical team needs it. The data output unit 107 is not limited to the above, and may include a common data output port (not shown) that can transmit/receive data in electric connection with a computer etc.

Figure 4:
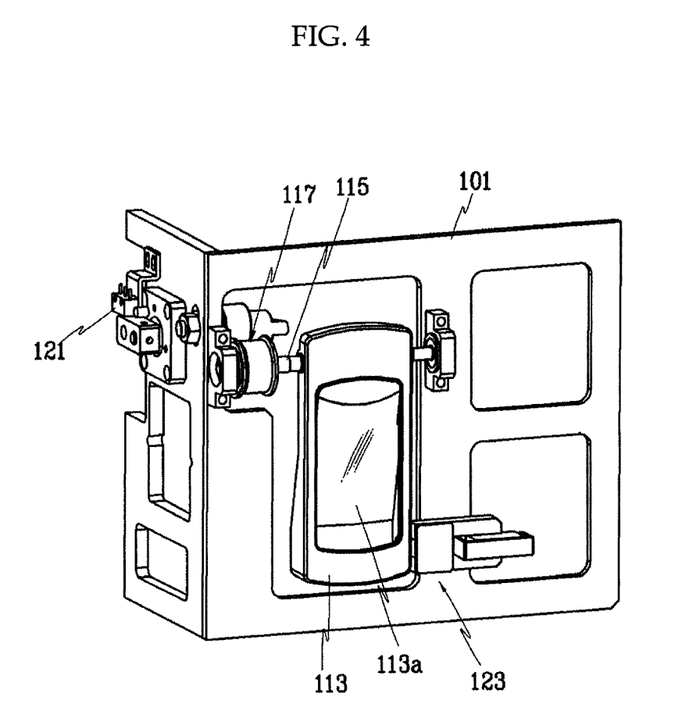
FIG. 4 is a view illustrating the main part inside an apparatus according to an exemplary embodiment of the present invention.

An introducing unit opening/closing cover 113 is hinged to the apparatus frame 101 such that it can rotate about a hinge shaft 115 as shown in FIG. 4. The blood introducing unit opening/closing cover 113 is provided with a magnifier 113a at the center. The magnifier 113a allows a user to easily observe components inside (a needle of the blood introducing unit that is described below). A power transmitting unit 117 that transmits torque from the hinge shaft 115 is fitted on the hinge shaft 115 of the blood introducing unit opening/closing cover 113. Although the blood introducing unit opening/closing cover 113 is connected to the hinge shaft 115 in this exemplary embodiment of the present invention, it is not limited to the above and may have other structures that can slide, depending on the design. Further, the blood introducing unit opening/closing cover 113 may be a lever for the blood introducing unit that opens/closes the blood introducing unit.

Figure 5:
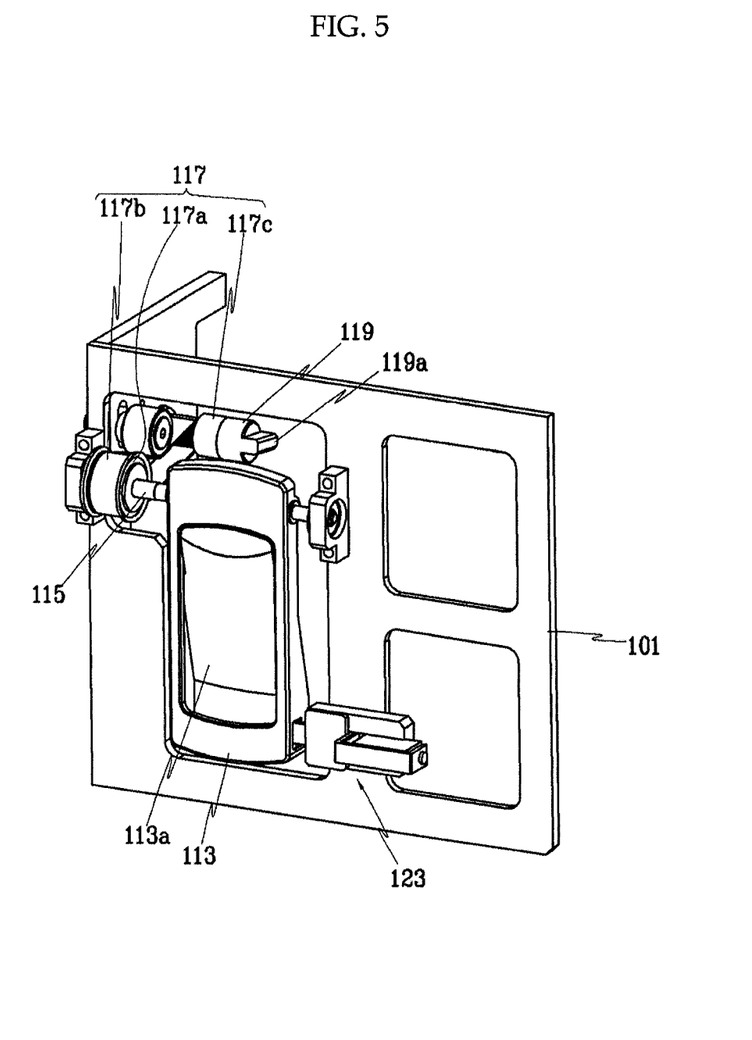
FIG. 5 is a view shown at a different angle of FIG. 4.

The power transmitting unit 117 opens/closes the blood introducing unit of the cartridge 300, which is described below, using the torque due to the operation of the blood introducing unit opening/closing cover 113. The power transmitting unit 117, as shown in FIG. 5, includes a driving pulley 115a connected with the hinge shaft 115, a belt 115b transmitting torque of the driving pulley, and a driven pulley 115c rotated by the torque transmitted from the belt 115b. A connector 119 for actuating the blood introducing unit of the cartridge 300 is connected to the shaft of the driven pulley 115c. It is preferable that the connector 119 has a protrusion 119a at an end to transmit a driving force to the blood introducing unit. The power transmitting unit 117 is not limited to the structure described in this exemplary embodiment of the present invention, and may include gears without a belt and may be changed to have an appropriate structure for transmitting power with rectilinear motion, and may also include various configurations.

The apparatus frame 101 is provided with a blood introducing unit opening/closing cover sensor (121, shown in FIG. 4) which detects opening/closing of the blood introducing unit opening/closing cover 113 and transmits a signal to the controller C. Further, the apparatus frame 101 is provided with a lock 123 that fixes the blood introducing unit opening/closing cover 113. The lock 123 may be a common lock that is electrically controlled by the controller C to lock the blood introducing unit opening/closing cover 113.

Figure 6:
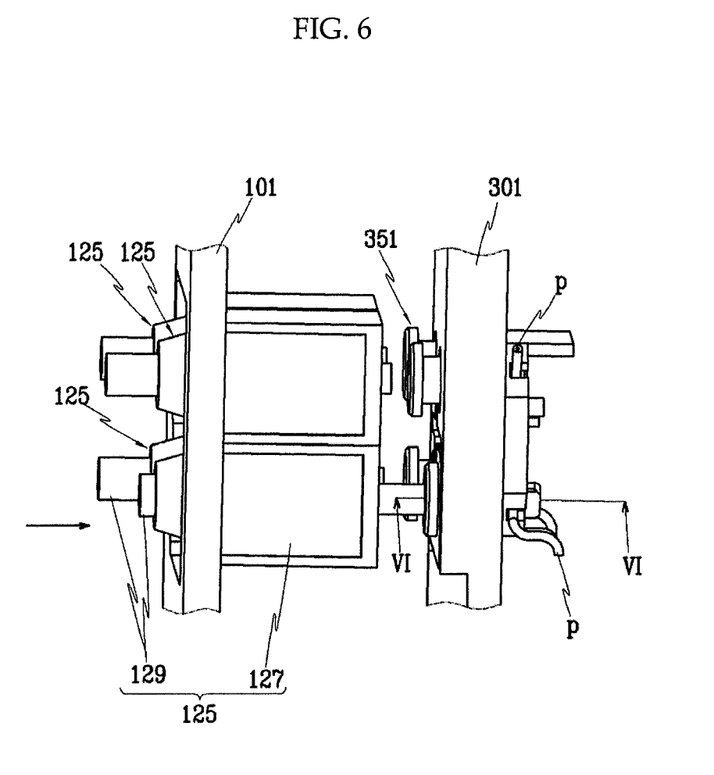
FIG. 6 is a view illustrating an opening/closing structure of a tubing according to an exemplary embodiment of the present invention.

Further, the apparatus frame 101 is provided with a driving unit 125 that supplies or blocks solutions, which are supplied to the cartridge 300, to a sensor card. The driving unit 125 is actuated by control of the controller (C). The driving unit 125 includes solenoid unit 127 and movable members 129 disposed and moved in the solenoid units 127. An exemplary embodiment provided with four driving units 125 is possible as shown in FIG. 6; however, the invention is not limited thereto and other numbers of driving units may be disposed, if needed by design. The driving unit 125 is controlled by the controller C, and a structure that can linearly move through the rotational motion may be applied to an exemplary embodiment of the present invention, as long as the movable member 129 moves to push a pressing member, which is described below. The driving unit 125 is provided with a driving unit operation sensor 131, which detects the operation of the driving unit 125 and transmits a signal to the controller C, at one side.

On the other hand, the apparatus frame 101 is provided with a cartridge door lock (133, shown in FIG. 1) which is controlled by the controller C to hold the cartridge 300 connected. A cartridge door lock sensor (135, shown in FIG. 1) that senses the locking status of the cartridge door lock 133 and transmits a signal to the controller may be provided.

Meanwhile, the apparatus frame 101 is provided with a solution transporting unit 137 that transports a solution by control of the controller C. The solution transporting unit 137 may have a structure including a rotator that is actuated by a motor and transports a solution while rotating in contact with a tubing. The solution transporting unit (137, shown in FIG. 1) is not limited to the above and other common means may be used, and a pump that can transport a solution may be used.

Further, the apparatus for analyzing blood chemistry is provided with a heater block (not shown) that has a heater for maintaining the temperature of the sensor card, which is described below. It is preferable that the heater is electrically connected to be actuated by the controller C.

Figure 7:
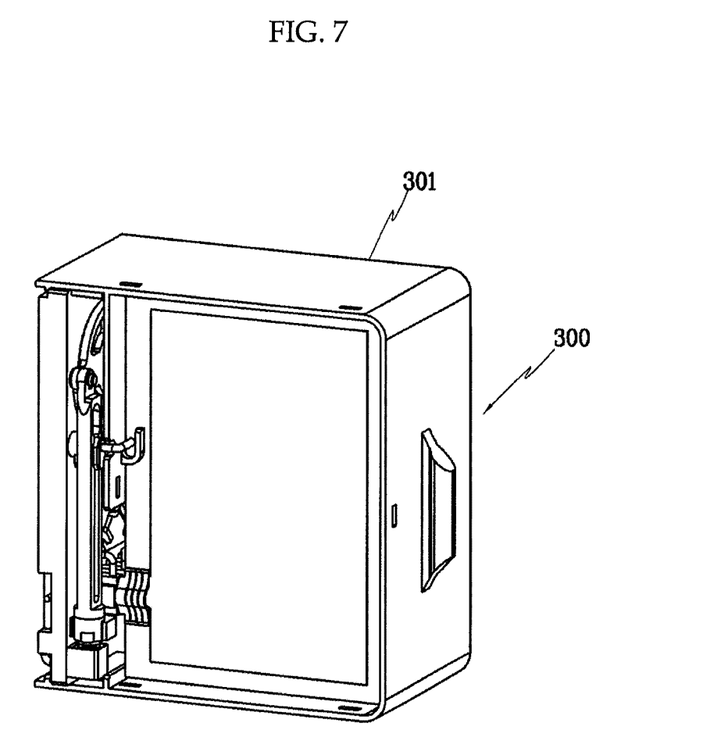
FIG. 7 is a perspective view showing a cartridge that is applied to the present invention.
Figure 8:
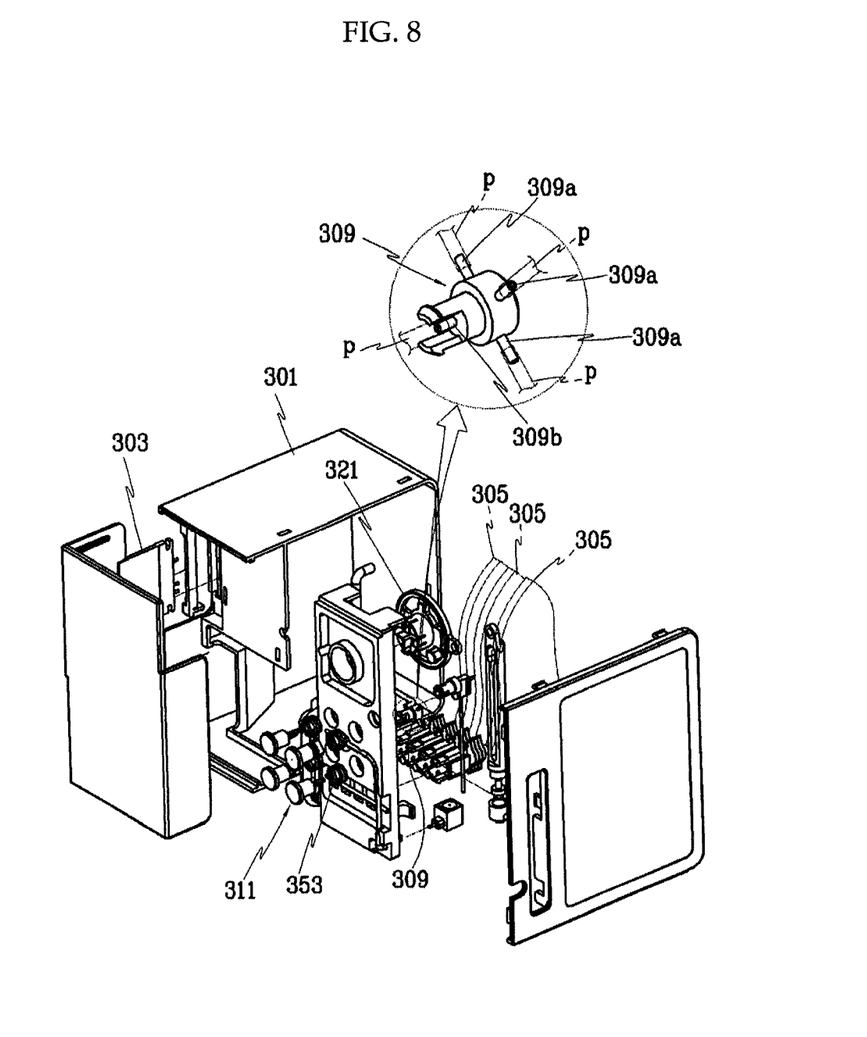
FIG. 8 is an exploded perspective view of FIG. 7.

FIG. 7 is a perspective view illustrating an exemplary embodiment of the invention, and FIG. 8 is an exploded perspective view of FIG. 7, showing the cartridge 300. The cartridge 300 includes a cartridge case 301, a sensor card 303, solution bags 305, a waste container (307, shown in FIG. 1), solution tubing connectors 309, a solution valve unit 311, and a blood introducing unit 313.

The cartridge case 301 is disposable and is replaced after being used for a predetermined period, and is formed of a substantially rectangular box with a space inside. The sensor card 303, the solution bags 305, the waste container 307, the solution tubing connectors 309, the solution valve unit 311, and the blood introducing unit 313 can be placed in the space of the cartridge case 301.

The sensor card 303 measures the concentrations of electrolytes, the partial pressures of gases, and the concentrations of metabolites, or volume ratio of red blood cells contained in blood of a specimen passing through the sensor card, and then transmits the measured values to the controller C. A common sensor card can be used as the sensor card 303. Although the sensor card 303 is connected with the cartridge case 301 in this exemplary embodiment of the present invention, the present invention is not limited thereto and the sensor car may be connected to the apparatus frame 101, and any other sensor cards may also be possibly used if they can be used in the apparatus for analyzing blood chemistry.

A variety of solutions are contained in the solution bags 305. The solutions are transported to the sensor card 303 and can be used as references for correcting the measured values of the concentrations of electrolytes, the partial pressures of gases, and the concentrations of metabolites the partial pressures of gases, and the concentrations of metabolites contained in blood. The solution bags 305 are connected to the solution connectors 309 through separate tubing (p). The solution bags 305 may be a common synthetic resin or aluminum bag.

Further, it is preferable that the cartridge case 301 is provided with the waste container 307 and a reference solution container 308. The waste container 307 is connected with the sensor card 303 by another tubing. The waste container 307 is a container where solutions used through the sensor card 303 are collected. The reference solution container 308 contains a solution having a function of QC (quality control) that periodically examines measurement of the sensor card 303. The values measured from the solution in the reference solution 308 are stored as data to allow a user to check the condition of the equipment.

The reference solution container 308 is connected with the sensor card 303 through another tubing (p). That is, the reference solution container 308, if needed, can directly supply the solution inside to the sensor card 303.

The solution tubing connectors 309 are connected with the solution bags 305 through the tubing (p). The solution tubing connectors 309 each have inlets 309a circumferentially disposed, and through which the solutions flows inside. The inlets 309a converge to an outlet 309b disposed at the center. The inlets 309a correspond to the solution bags 305 and are connected with each other to always transport the solutions to the outlet 309b through the tubing (p). That is, the inlets 309a of the solution tubing connector 309 have a one-to-one connection with the solution bags 305 such that the solutions are always transported. The outlet 309b is connected to a tubing (p) such that the solutions flowing inside through the inlets 309a are transported to the blood introducing unit 313.

Figure 9:
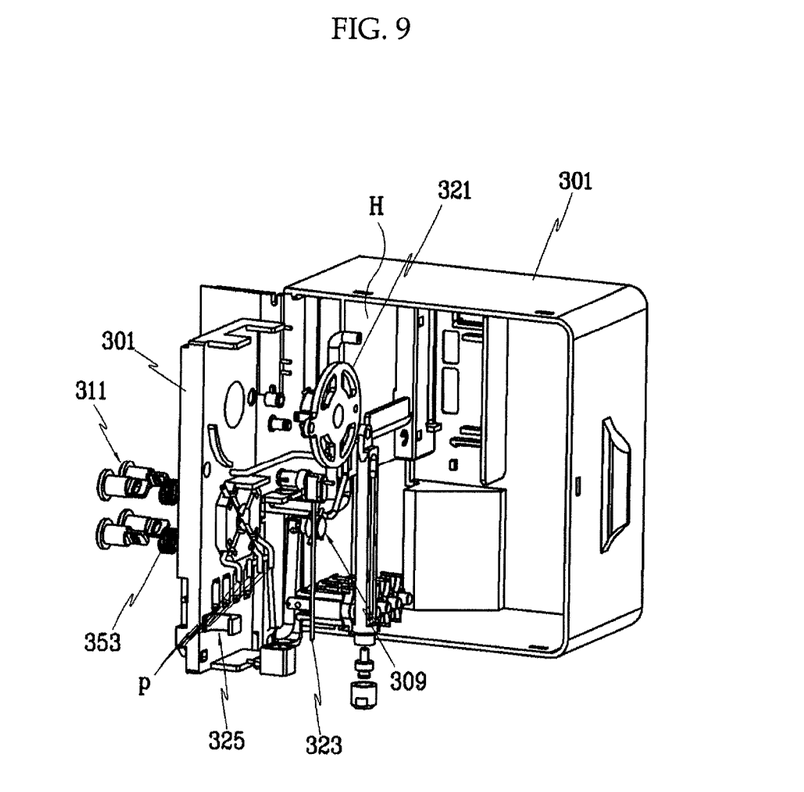
FIG. 9 is an exploded view showing a portion of the cartridge that is applied to the present invention.

The blood introducing unit 313 transports the specimen to the sensor card 303, or transports the solution passing through the solution tubing connector 309 or the reference solution to the sensor card 303. The blood introducing unit 313 includes a rotator 321 that is connected with the protrusion formed at the end of the connector 119 of the power transmitting unit 117, which was described in connection with the main body 100, and rotates, a needle 323 connected to the rotator 321, and another tubing (p) through which blood flowing inside through the needle 323 or solutions are transported to the sensor card 303. The blood introducing unit 313 has a structure in which the needle 323 protrudes outside or is received in a guide (325, shown in FIG. 9) by the rotation of the blood introducing unit opening/closing cover 113. That is, when the needle 323 protrudes outside due to the rotation of the rotator 321, blood is supplied and transported to the sensor card 303, whereas when the needle 323 is received inside due to the rotation of the rotator 321, it is connected to the tubing (p) connected to the outlet 309b of the solution tubing connector 309, such that the solutions are supplied and transported to the sensor card 303. The blood introducing unit 313 may have a common structure that is known and used in the art. The structure of the blood introducing unit 313 described in this exemplary embodiment of the present invention is not limited to the above, and rectilinear motion, such as a slide, can be applied, in addition to the rotation of the rotator. Further, the blood introducing unit 313 has a guide 325 with a semicircular groove inside the cartridge to be received at a predetermined position in the drawings, but is not limited thereto and may have rolling members, such as balls, and a plurality of grooves where the balls are inserted and fixed at predetermined positions such that the blood introducing unit 313 can move within a predetermined section. Meanwhile, the tubings (p) are in close contact with the solution transporting unit 137 and the solution is transported by the operation of the transporting unit 137. It is preferable that the tubings (p) are made of synthetic resin having large elasticity.

Figure 10:
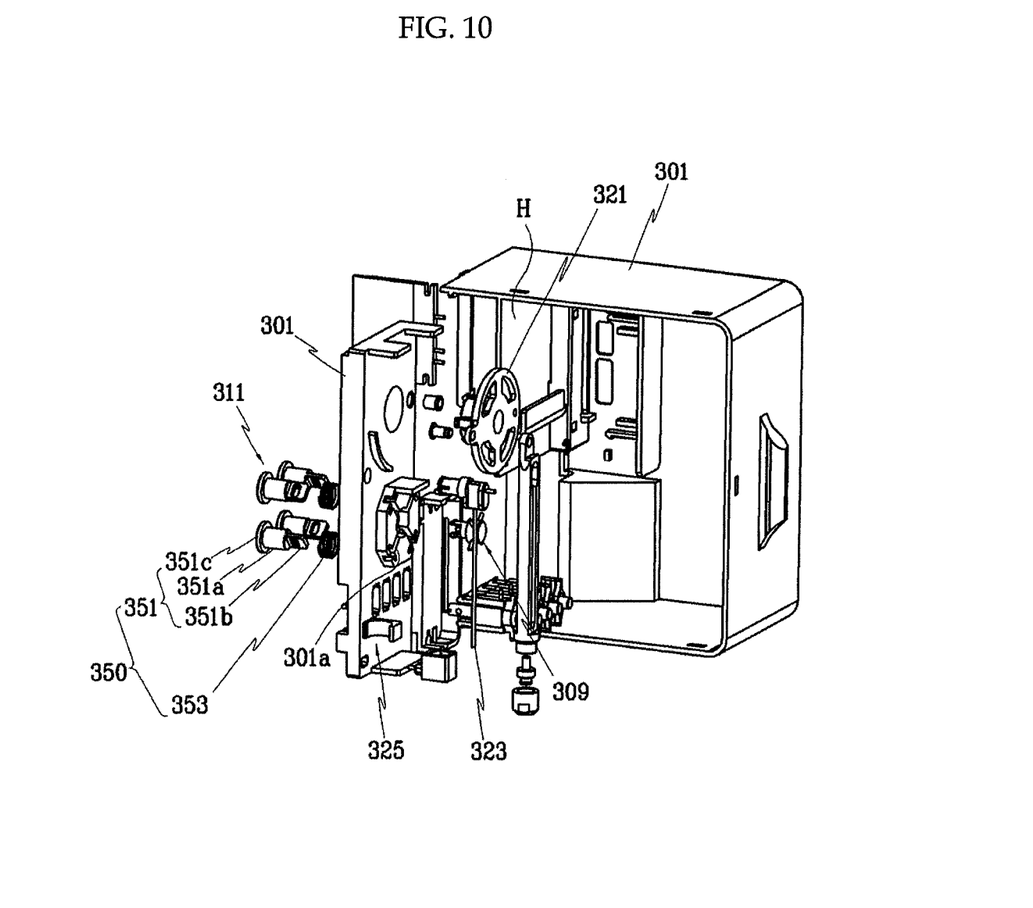
FIG. 10 is a view showing the inside of the cartridge that is applied to the present invention.
Figure 11:
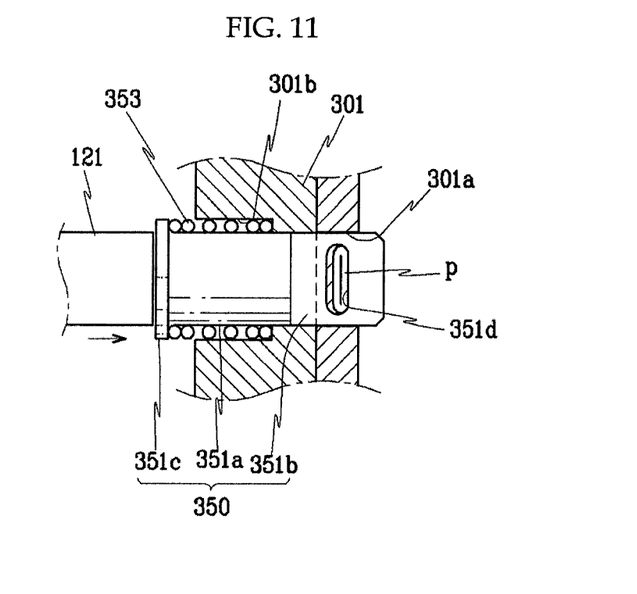
FIG. 11 is a cross-sectional view taken along the line VI-VI of FIG. 6.

The solution valve unit 350, as shown in FIG. 10 and FIG. 11, allows or blocks a flow of a solution to the sensor card 303 by opening or closing the tubings (p) disposed between the solution bags 305 and the solution tubing connectors 309. The solution valve unit 350 includes pressing members 351 and elastic members 353. The pressing members 351 each include a cylindrical body 351a, an extension 351b extending from the body 351a, and a head 351c formed at the end opposite to the extension 351b. A tubing insertion hole 351d is formed through the extension 351b at the center of the body 351a in the circumferential direction. The extension 351b may be relatively flat such that a slit 301a of the cartridge case 301 can be inserted and slide therein. The body 351a can be inserted and slid in a hole 301b of the case 301. The elastic member 353 is disposed in the separating direction from the case 301 while being elastically supported by the head 351c of the pressing member 351 and the case 301. It is preferable that the elastic member 353 is a compression coil spring. However, the elastic member 353 may be any one that can move the pressing member 351 in one direction. That is, the tubing (p) made of synthetic resin is pushed in the tubing insertion hole 351d of the pressing member 351 when an elastic force is applied by the elastic member 353, such that the movement of the solutions is restricted. As the pressing members 351 are pressed by the movable members 129 of the driving unit 125 and the elastic members 353 are pushed, the pressure applied to the tubing (p) is released and the solutions correspondingly flow.

On the other hand, it is preferable that the controller that receives and processes a signal generated from the sensor card and the controller that controls the solution transporting unit and driving unit are electrically separated. That is, it is preferable that independent power is provided for the processing unit of the signal detected by the sensor card and an actuating unit of a pump-solenoid to avoid electrical interference, and independent isolation circuits are applied to the input/output signal unit.

Further, it is preferable that the signals detected in the controller, which receives and processes the signals generated from the sensor card, are electrically classified according to the types. In other words, it is preferable that electrical isolation circuits are applied to avoid interference between the signals detected by the sensor card, that is, independent sensing signals for each measuring item of electrolytes, the partial pressures of gases, and the concentrations of metabolites, and volume ratio of the red blood cells, or electrical interference.

Figure 13:
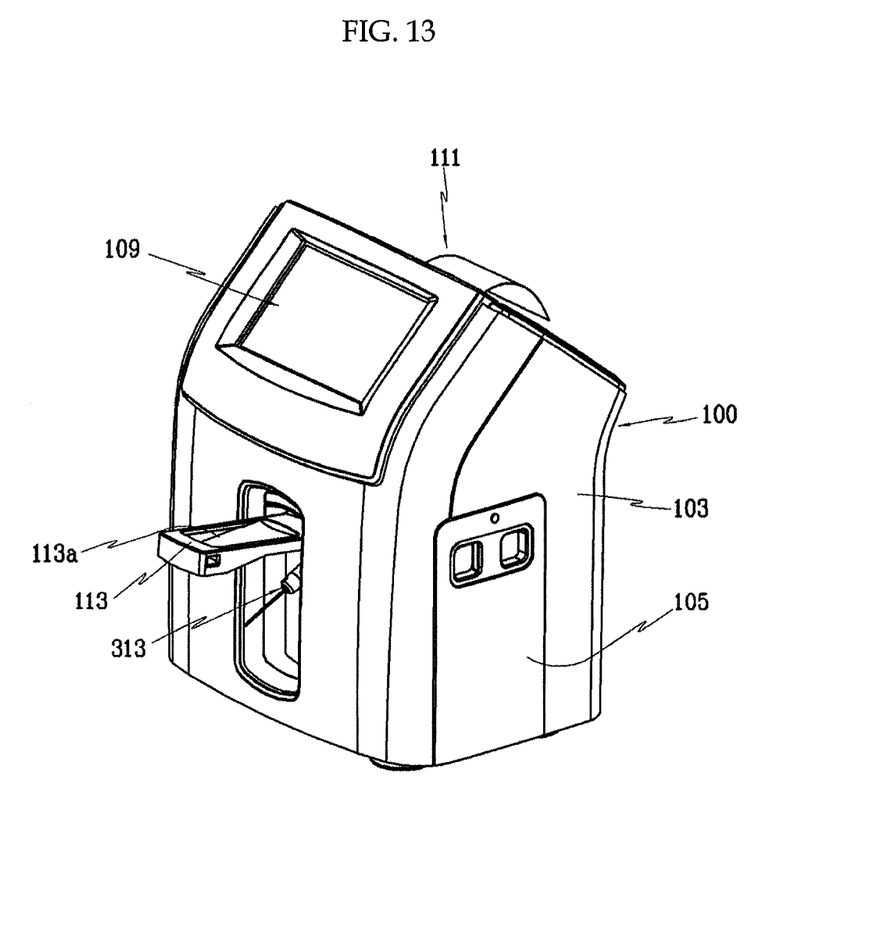
FIG. 13 is a view illustrating the operation of an exemplary embodiment of the present invention.
Figure 14:
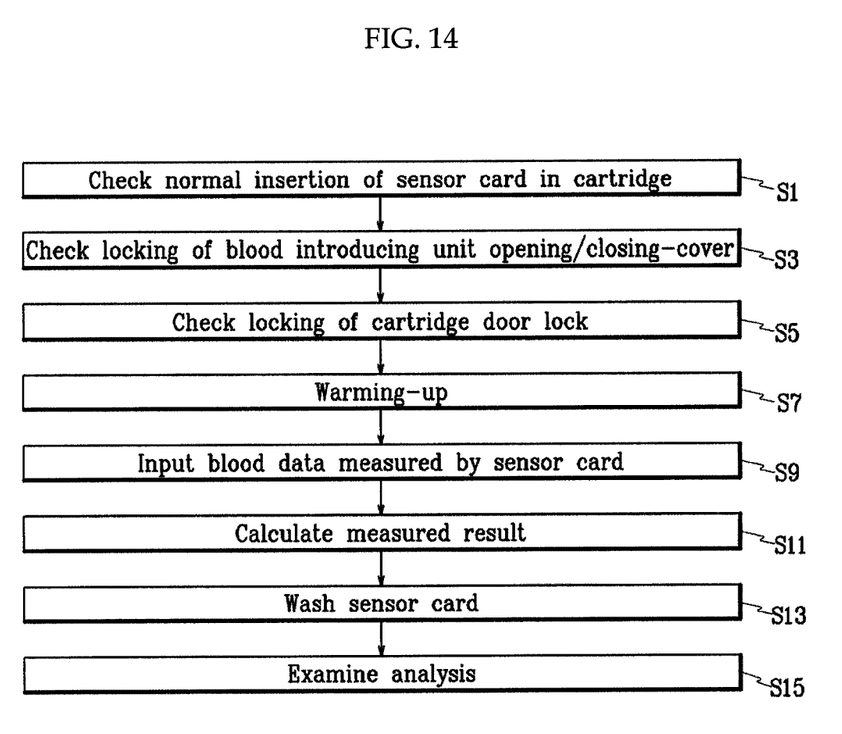
FIG. 14 is a flowchart illustrating the operation of an exemplary embodiment of the present invention.

The operating process of an exemplary embodiment of the present invention having the above configuration is described in detail with reference to FIG. 1, FIG. 13, and FIG. 14, and other accompanying drawings.

Figure 12:
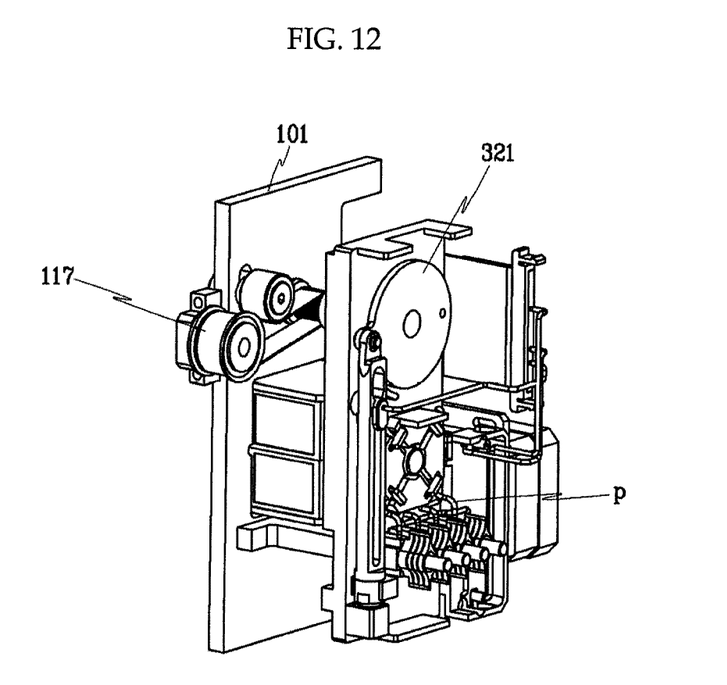
FIG. 12 is a detailed view showing the main part of an exemplary embodiment of the present invention.

First, a user opens the cartridge door 105 and inserts the cartridge 300 into the main body 100. The user then closes the cartridge door 105. The controller C checks whether the sensor card 303 is normally inserted in the cartridge 300 (S1). The controller C makes the lock for the blood introducing unit opening/closing cover 123 normally lock the blood introducing unit opening/closing cover 113. The controller C receives a signal generated by the blood introducing unit opening/closing cover sensor 121 detecting that the lock for the blood introducing unit opening/closing cover 123 is locked (S3). Further, the controller C locks the cartridge door 105 by the cartridge door lock 133. Similarly, the controller C receives a signal generated by the cartridge door lock sensor 135 detecting that the cartridge door lock 133 is locked (S5). A preliminary warm-up for analysis is performed after steps S1, S3, and S5 (S7). In the warm-up, reference data is first measured by alternatively transporting the solutions in the solution bags 305. The reference data is used for correcting data measured from blood in a next process. Transportation of the solutions is described hereafter. The controller C controls the driving unit 125 to control the movable member 129 that can open the tubing (p) connected to a desired solution bag1 305. The movable member 129, as shown in FIG. 6, supplies a solution and presses the pressing member 351 of the block unit 350 while moving in the arrow direction. The pressing member 351 correspondingly moves in the arrow direction against the elastic force of the elastic member 353. The pressing member 351 releases the pressure applied to the tubing (p). As a result, the solution is transported through the tubing (p). The solution is transported to the sensor card 303 through the blood introducing unit 313. An electric signal generated by the transportation of the solution to the sensor card 303 is transmitted to the controller C. Similarly, the sensor card 303 detects electric signals of the solutions in the other solution bags 305, if needed. The solution supplied to the sensor card 303 is transported to the waste container 307 and stored therein. When it is ready to measure blood, the controller C controls the lock for the blood introducing unit opening/closing cover 123 to be open. The user softly pulls the blood introducing unit opening/closing cover 113 by hand. The blood introducing unit opening/closing cover 113 correspondingly turns and torque is transmitted through the power transmitting unit 117. That is, as the blood introducing unit opening/closing cover 113 rotates, the hinge shaft 115 rotates, and as the hinge shaft 115 rotates, the torque of the driving pulley 117*a* is transmitted to the driven pulley 117*c* through the belt 117*b*. The torque of the driven pulley 117*c* is transmitted to the connector 119. The torque transmitted to the connector 119 rotates the rotator (321, shown in FIG. 12) of the cartridge 300. As the rotator rotates 321, the needle 323 rotates and the end protrudes outside. The user then contacts a blood sample to the end of the needle. Thereafter, the controller C controls the solution transporting unit 137 to transport the blood sample into the sensor card 303. The controller C informs the user that he/she can close the blood introducing unit opening/closing cover 113 through the display. The user softly closes the blood introducing unit opening/closing cover 113. The controller C can maintain the lock by actuating the lock for the blood introducing unit opening/closing cover 123. Further, the sensor card 303 detects electrical signals corresponding to the concentrations of electrolytes, the partial pressures of gases, and the concentrations of metabolites, or the volume ratio of the red blood cells in the blood, and transmits the signals to the controller C (S9). The controller C calculates the result of the analysis of the measured substances on the basis of the measured data from the electric signals of the solutions in the solution bags 305 (S9), and can store the data in a storage (not shown) or output it to the data output unit 107. Thereafter, the sensor card 303 is washed by the solution in the solution bags 305 (S13). Washing the sensor card 303 is done when the solution in the solution bags 305 flows into the waste container 307 through the sensor card 303 by the solution transmitting unit 137 actuated by the controller C. The controller C performs analysis examination (S15).

According to the exemplary embodiment of the present invention, since the solution bags 305 have one-to-one connection with the solution tubing connectors 309, even though different solutions are repeatedly passed, they do not leak outside. Accordingly, it is possible to improve accuracy of the sensed data and the commercial value. Further, according to an exemplary embodiment of the present invention, it is possible to transport two or more solutions by actuating two or more movable members, such that availability can be improved. Further, according to an exemplary embodiment of the present invention, it is possible to achieve an apparatus for analyzing blood chemistry that has a structure that uses manual sampling, by using a cartridge including a sensor card, tubing, and a solution, such that the electrically-actuated units are not needed. Therefore, it is possible to reduce manufacturing cost and power consumption.

Further, according to an exemplary embodiment of the present invention, the apparatus has a simple structure, such that a medical team can conveniently use the apparatus anywhere they need without requiring a space.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. An apparatus for analyzing blood chemistry, comprising:
   an apparatus frame having a compartment;
   a cartridge that is inserted into the compartment of the apparatus frame and includes solution bags that contain solutions, a solution valve unit that allows or blocks the flow of the solution, and a blood introducing unit;
   a sensor card that is disposed in the cartridge or in the apparatus frame and measures the concentrations of electrolytes, the partial pressures of gases, the concentrations of metabolites, or the volume ratio of the red blood cells contained in blood supplied through the blood introducing unit;
   a controller that receives signals generated from the sensor card and processes the signals;
   a lever for the blood introducing unit that is fastened by a hinge to the apparatus frame such that the lever for the blood introducing unit rotates about a hinge shaft;
   a power transmitting unit that is provided at the apparatus frame and that opens or closes the blood introducing unit using torque due to an operation of the lever for the blood introducing unit;
   a solution transporting unit that is provided at the apparatus frame and transports the solutions in the solution bags; and
   a driving unit;
   wherein each driving unit includes
      a solenoid unit that is controlled by the controller; and
      a movable member that moves based on electrical operation of the solenoid unit and that actuates the solution valve unit of the cartridge, the movable member opening or closing a tubing to flow of the solutions;
   wherein the apparatus frame includes a cartridge door having a cartridge door lock that locks the cartridge door to the apparatus frame and a cartridge door lock sensor that senses a locking status of the cartridge door; and
   wherein the apparatus frame includes a lever lock that locks the lever for the blood introducing unit and a lever lock sensor that senses a locking status of the lever.

2. The apparatus for analyzing blood chemistry of claim 1, further comprising
data output units that output data processed by the controller,
wherein the data output units include a display and a printer, both of which are integrated in the apparatus.

3. The apparatus for analyzing blood chemistry of claim 1, wherein a part of the controller that receives signals generated from the sensor card and processes the signals is electrically isolated from a part of the controller that controls the solution transporting unit and the driving unit.

4. The apparatus for analyzing blood chemistry of claim 1, wherein the signals generated from the sensor card that the controller receives and processes are electrically isolated between the signals depending on the type of the signals.

5. The apparatus for analyzing blood chemistry of claim 1, wherein the cartridge door is fastened by a hinge to the apparatus frame and the cartridge door lock sensor senses the locking status of the door lock and transmits a sensed signal to the controller.

6. The apparatus for analyzing blood chemistry of claim 1, wherein the lever lock locks the lever for the blood introducing unit and a sensing unit senses the locking status of the lever lock and transmits a sensed signal to the controller.

7. The apparatus for analyzing blood chemistry of claim 1, wherein the apparatus frame is provided with a sensing unit that detects the operation of the driving unit and transmits a detected signal to the controller.

8. The apparatus for analyzing blood chemistry of claim 1, wherein the lever for the blood introducing unit is the cover for the blood introducing unit that is composed of a magnifier at the center thereof.

9. The apparatus for analyzing blood chemistry of claim 1, wherein the apparatus frame is provided with a heater block equipped with a heater to maintain the temperature of the sensor card constant.

10. The apparatus for analyzing blood chemistry of claim 1, wherein the cartridge is provided with a waste container that is connected with the sensor card through tubing.

* * * * *